United States Patent
Safabash et al.

(10) Patent No.: US 11,000,368 B2
(45) Date of Patent: *May 11, 2021

(54) ATRAUMATIC IOL INSERTION CARTRIDGE OPENING

(71) Applicant: Johnson & Johnson Surgical Vision, Inc., Santa Ana, CA (US)

(72) Inventors: Jason H. Safabash, Mission Viejo, CA (US); David W. Gaylord, Santa Ana, CA (US); Kevin Springer, Santa Ana, CA (US)

(73) Assignee: Johnson & Johnson Surgical Vision, Inc., Santa Ana, CA (US)

( * ) Notice: Subject to any disclaimer, the term of this patent is extended or adjusted under 35 U.S.C. 154(b) by 192 days.

This patent is subject to a terminal disclaimer.

(21) Appl. No.: 16/257,010

(22) Filed: Jan. 24, 2019

(65) Prior Publication Data

US 2019/0151080 A1    May 23, 2019

Related U.S. Application Data

(63) Continuation of application No. 14/195,622, filed on Mar. 3, 2014, now Pat. No. 10,265,164.

(Continued)

(51) Int. Cl.
*A61F 2/16* (2006.01)

(52) U.S. Cl.
CPC .................. *A61F 2/1678* (2013.01)

(58) Field of Classification Search
CPC ............ A61B 17/3417; A61B 17/3468; A61B 2017/3454; A61F 2/1662; A61F 2/1667;
(Continued)

(56) References Cited

U.S. PATENT DOCUMENTS

| 4,490,139 A | 12/1984 | Huizenga et al. |
| 4,919,130 A * | 4/1990 | Stoy ...................... A61F 2/1664 606/107 |

(Continued)

FOREIGN PATENT DOCUMENTS

| BE | 720694 A | 2/1969 |
| WO | 2011101683 A1 | 8/2011 |
| WO | 2012081419 A1 | 6/2012 |

OTHER PUBLICATIONS

International Search Report and Written Opinion for Application No. PCT/US2014/019987, dated May 9, 2014, 11 pages.

*Primary Examiner* — Ryan J. Severson
(74) *Attorney, Agent, or Firm* — Johnson & Johnson Surgical Vision, Inc.

(57) ABSTRACT

This intraocular lens (IOL) injector cartridge has a proximal opening in a main body for receiving an IOL. The main body has a lumen that extends longitudinally to a distal end having an opening smaller than the IOL. Passage through the lumen compresses or rolls the IOL so that when the distal end is inserted through a small incision in the eye the IOL can be expelled into the capsular bag. The distal end of the cartridge is beveled with a leading tip in front of a trailing heel. The characteristics of the beveled end are such that damage to the IOL is reduced. The bevel may be straight or curved and includes a distal face defined by the thickness of the distal end between the lumen and an exterior surface. The distal face may be flush with the bevel or chamfered. An inner corner angle between the distal face and the lumen is ≥60° to reduce the chance of scratching the IOL as it passes out of the distal opening.

19 Claims, 7 Drawing Sheets

Related U.S. Application Data

(60) Provisional application No. 61/773,496, filed on Mar. 6, 2013.

(58) Field of Classification Search
CPC ...... A61F 2/167; A61F 2/1678; A61F 2/1691; A61F 9/007
See application file for complete search history.

(56) References Cited

U.S. PATENT DOCUMENTS

| | | | |
|---|---|---|---|
| 5,536,259 A | 7/1996 | Utterberg et al. | |
| 5,575,780 A | 11/1996 | Saito et al. | |
| 5,788,679 A | 8/1998 | Gravlee | |
| 5,810,834 A | 9/1998 | Heyman et al. | |
| 5,876,406 A * | 3/1999 | Wolf | A61F 2/1664 606/107 |
| 5,928,245 A * | 7/1999 | Wolf | A61F 2/1678 606/107 |
| 6,056,757 A * | 5/2000 | Feingold | A61F 2/1664 606/107 |
| 6,214,015 B1 * | 4/2001 | Reich | A61F 2/1664 606/107 |
| 6,248,111 B1 * | 6/2001 | Glick | A61F 2/1675 606/107 |
| 6,361,504 B1 | 3/2002 | Shin | |
| 6,447,520 B1 * | 9/2002 | Ott | A61F 2/1678 606/107 |
| 6,506,195 B2 * | 1/2003 | Chambers | A61F 2/1664 606/107 |
| 7,063,681 B1 | 6/2006 | Peery et al. | |
| 7,329,242 B2 | 2/2008 | Peery et al. | |
| 7,670,299 B2 | 3/2010 | Beckman et al. | |
| 8,382,769 B2 * | 2/2013 | Inoue | A61F 2/1678 606/107 |
| 8,460,311 B2 * | 6/2013 | Ishii | A61F 2/1678 606/107 |
| 10,265,164 B2 * | 4/2019 | Safabash | A61F 2/1678 |
| 2002/0165610 A1 * | 11/2002 | Waldock | A61F 2/1664 623/6.12 |
| 2002/0188247 A1 | 12/2002 | Peery | |
| 2006/0167466 A1 | 7/2006 | Dusek | |
| 2008/0300507 A1 | 12/2008 | Figueredo et al. | |
| 2008/0312661 A1 | 12/2008 | Downer et al. | |
| 2014/0135782 A1 * | 5/2014 | Valle | A61F 2/1691 606/107 |
| 2014/0257316 A1 | 9/2014 | Safabash et al. | |
| 2019/0151080 A1 * | 5/2019 | Safabash | A61F 2/1678 |

* cited by examiner

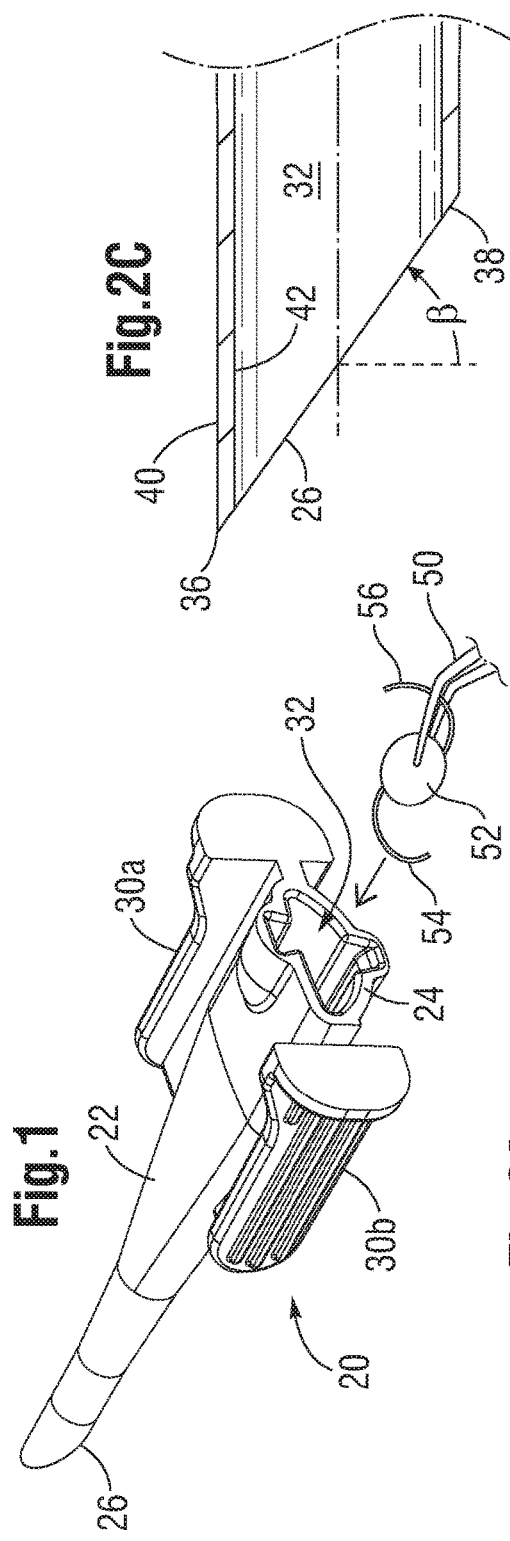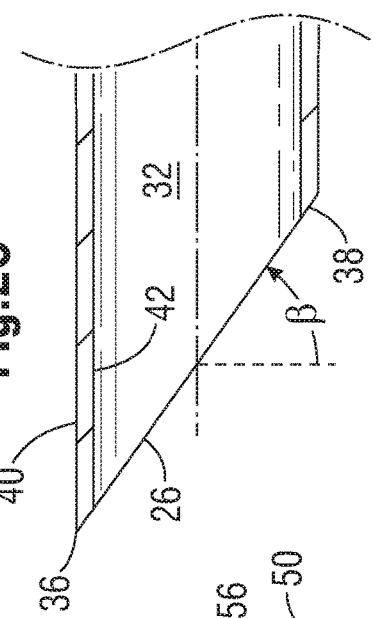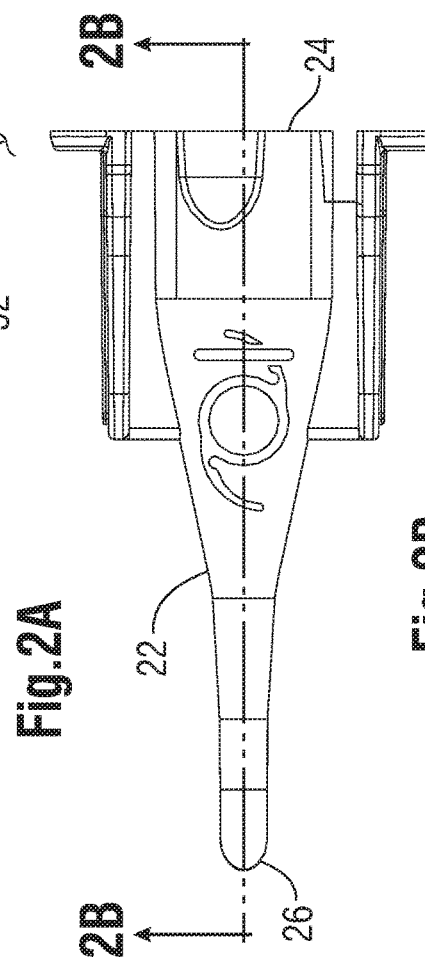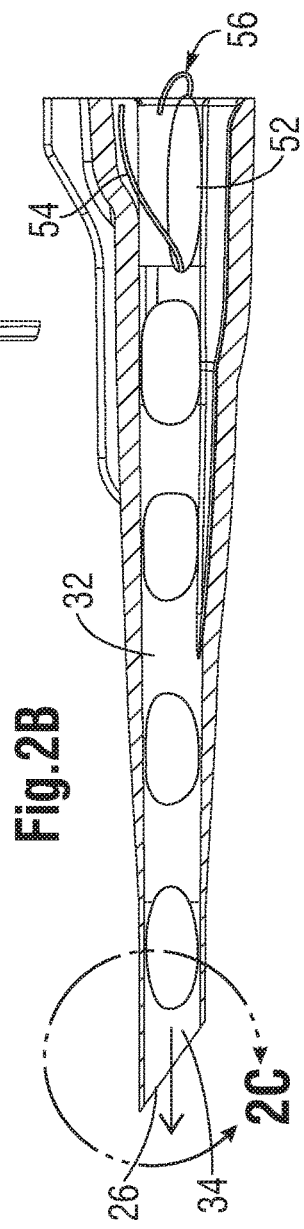

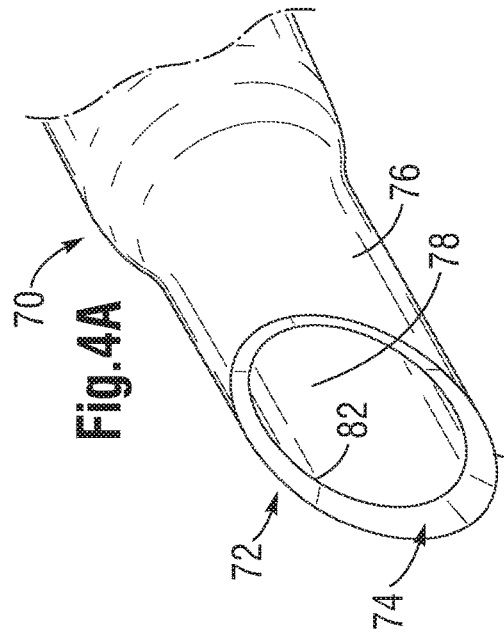
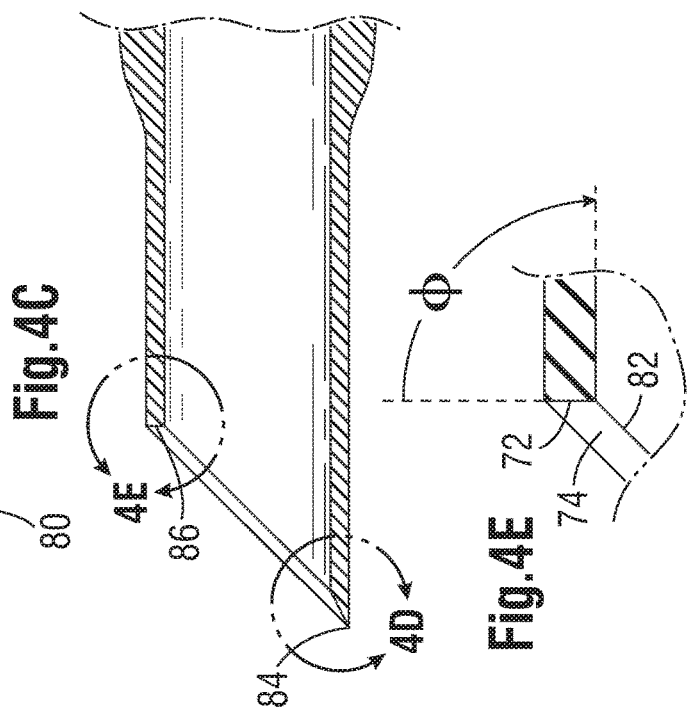
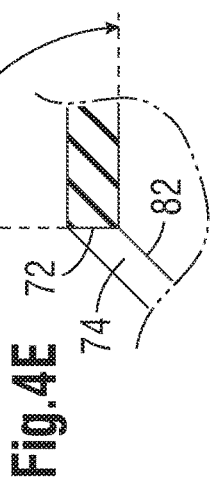
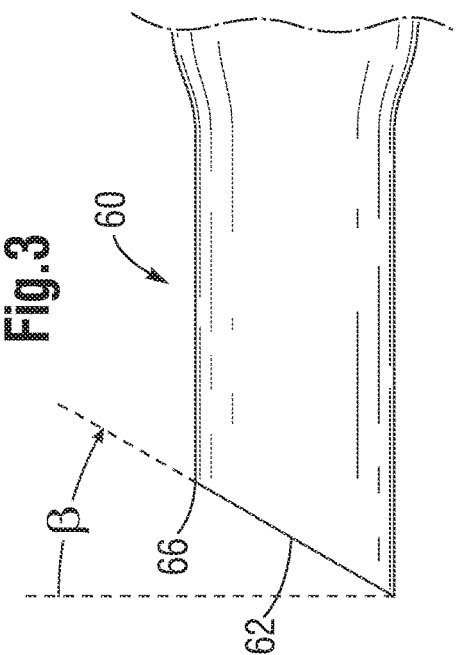
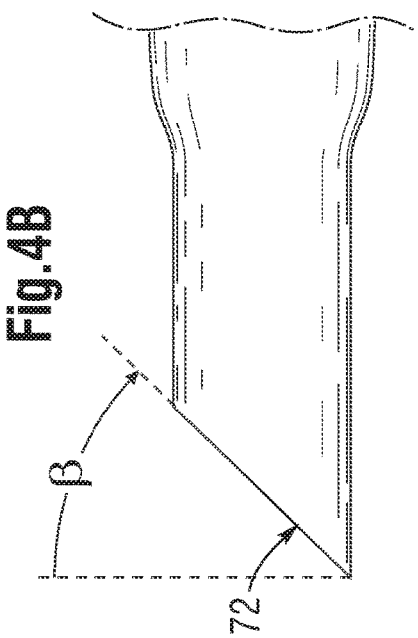
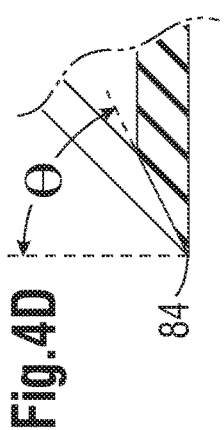

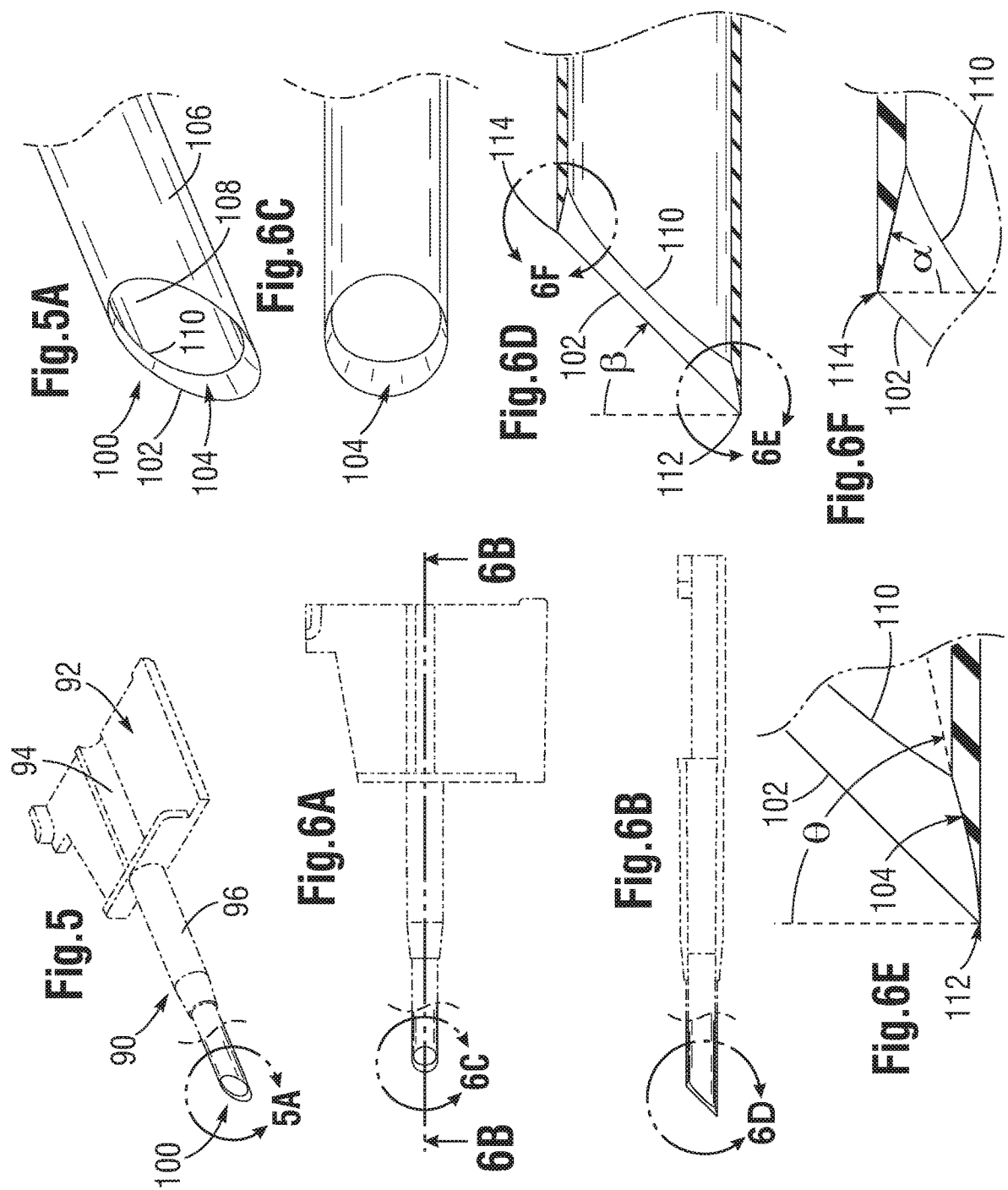

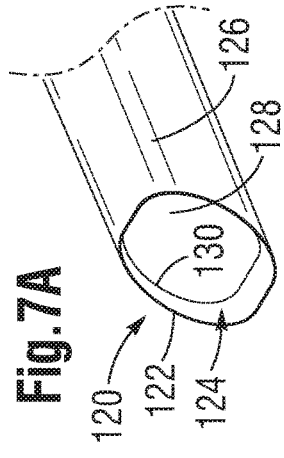
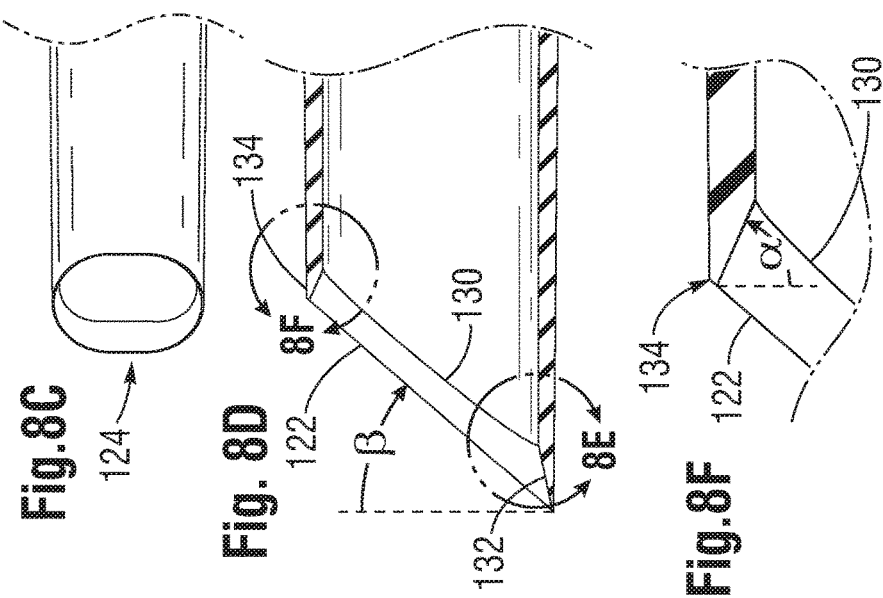
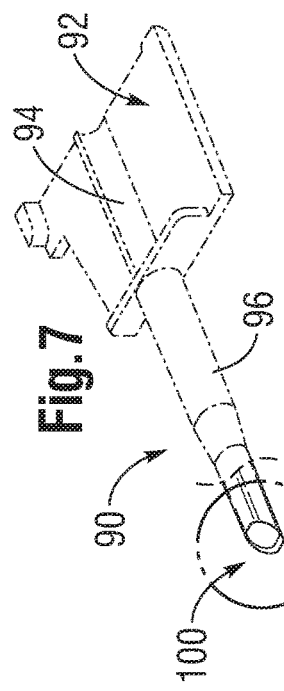
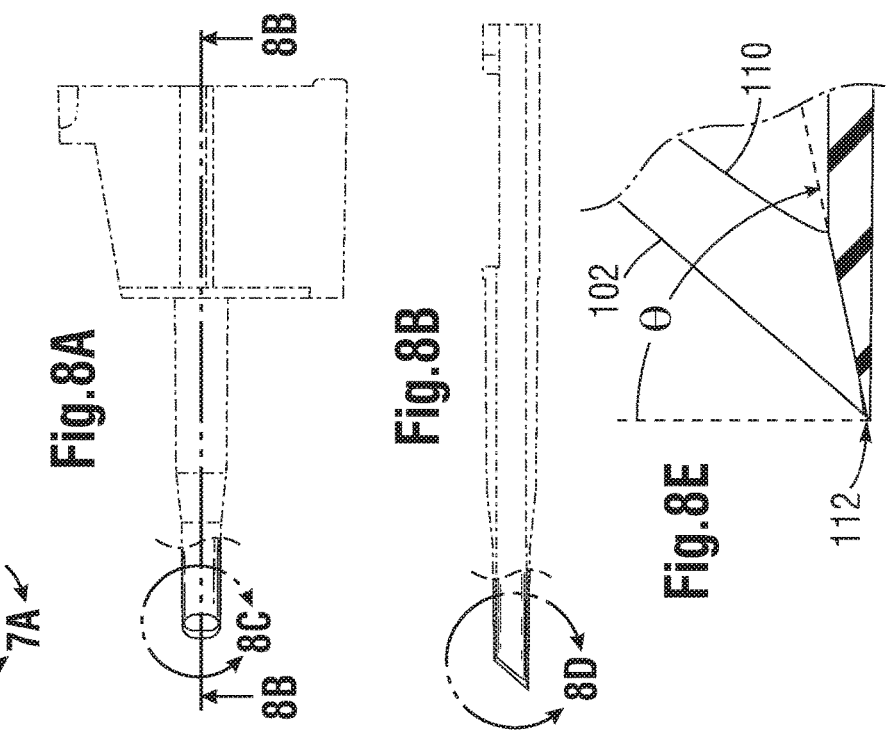

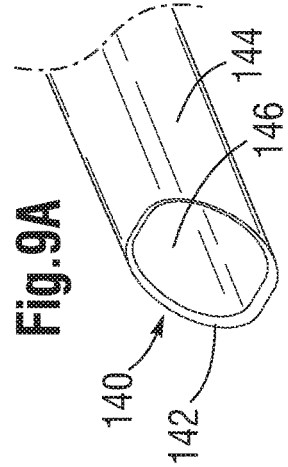
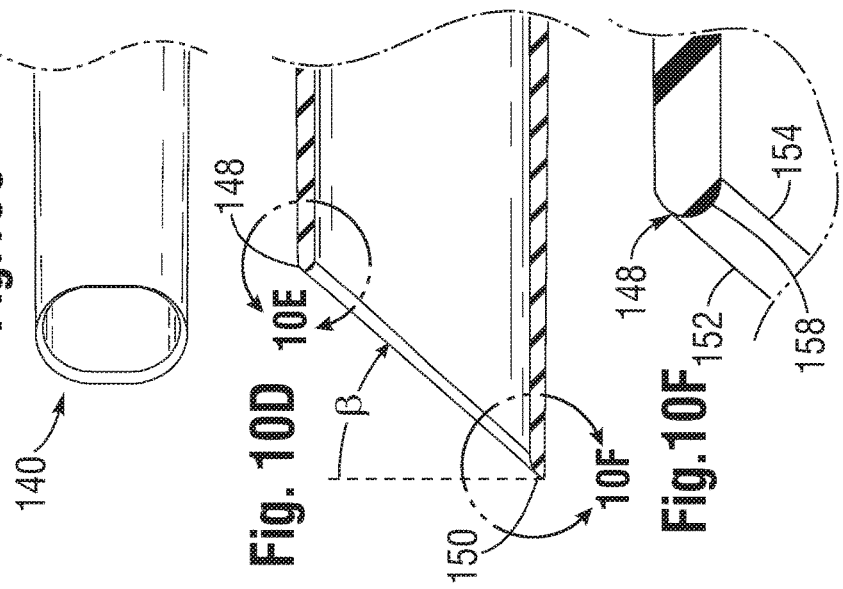
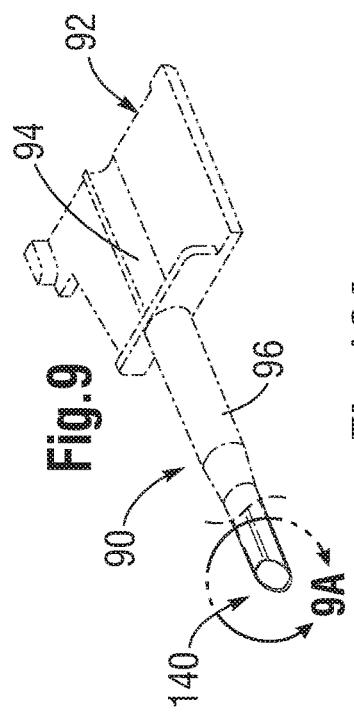
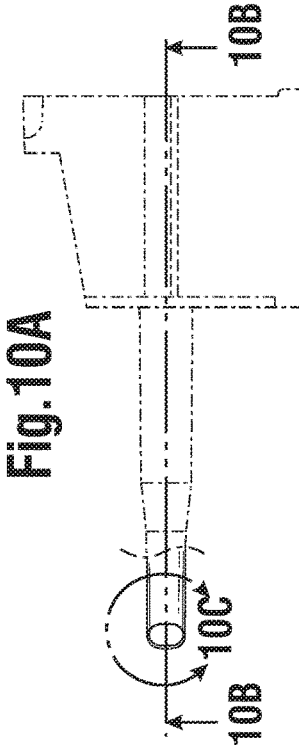
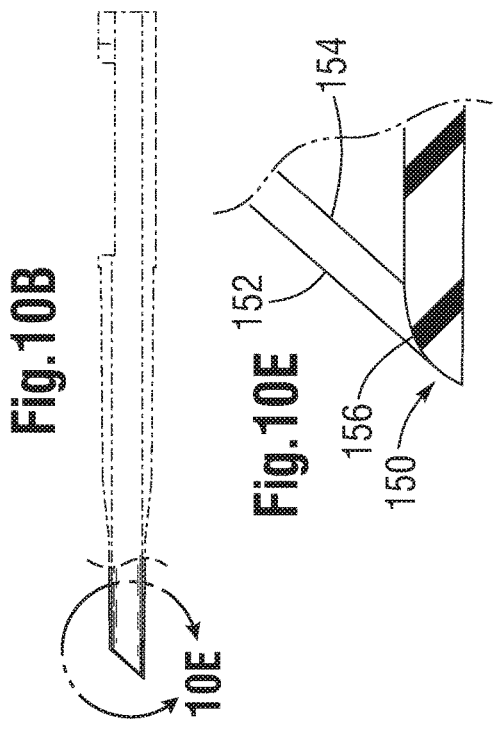

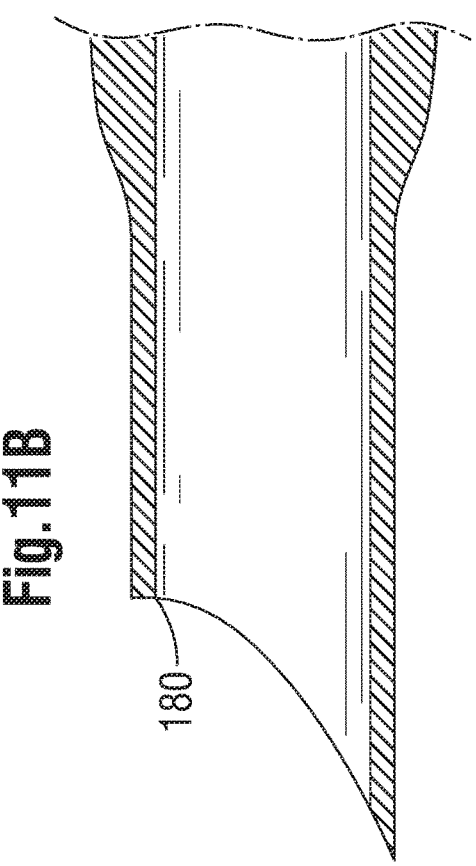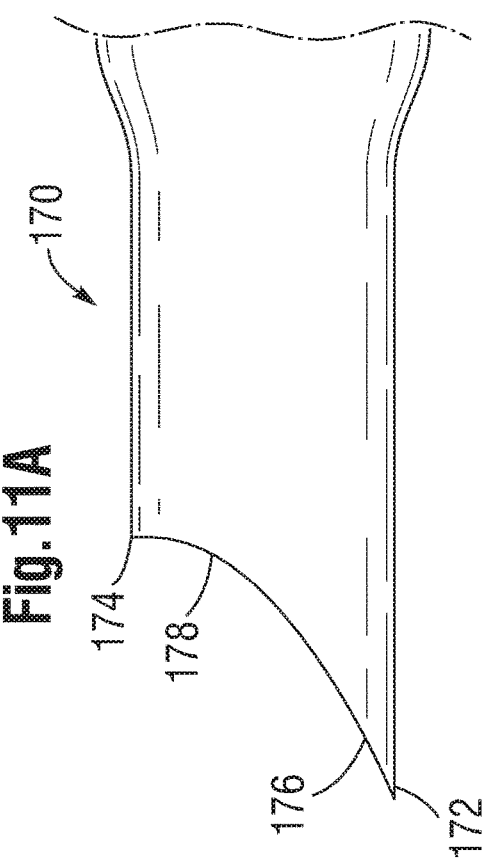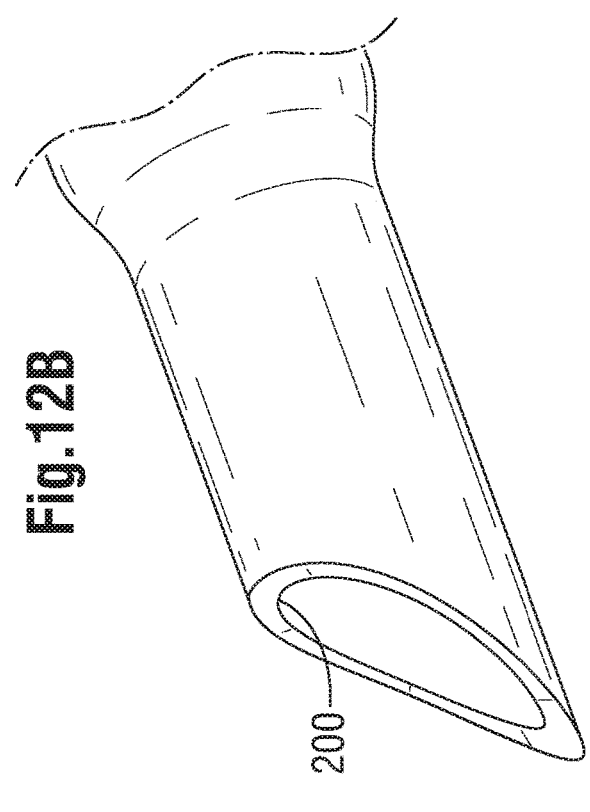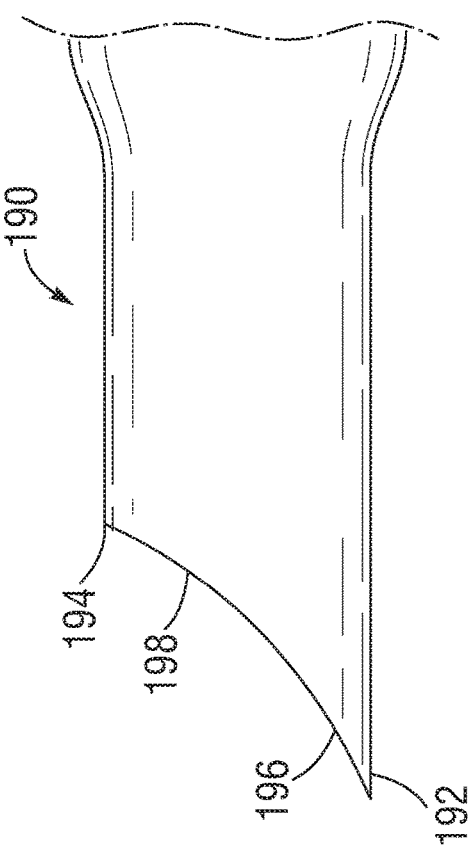

ATRAUMATIC IOL INSERTION CARTRIDGE OPENING

CROSS REFERENCES TO RELATED APPLICATIONS

This application is a continuation of U.S. application Ser. No. 14/195,622 filed on Mar. 3, 2014, which claims priority to U.S. provisional application No. 61/773,496 filed on Mar. 6, 2013, the entire contents of which are incorporated herein by reference.

FIELD OF THE INVENTION

The present invention relates to devices for delivering an intraocular lens (IOL) into an eye and, more particularly, to an atraumatic IOL injector cartridge tip.

BACKGROUND OF THE INVENTION

It is estimated that at least about 42% of Americans between the ages of 52 and 64 and 73% of Americans between the ages of 65 and 74 get cataracts. A cataract is a clouding of the eye's lens that impairs a person's vision and, if left untreated, causes blindness. As a result, each year approximately 1.4 million people in the United States alone undergo cataract surgery, whereby the clouded lens is removed and replaced with an intraocular lens (IOL) implant.

A typical IOL includes an optic or lens body for focusing light toward the retina of the eye. In addition, the IOL also includes one or more fixation members or haptics extending outward from the optic for securing and centering the IOL in the desired position within the chamber of the eye. The IOL is implanted directly into the eye through a small incision in a way that reduces trauma and expedites post-surgery healing. To fit through this small incision, modern IOLs are designed to be deformed, e.g., rolled, folded or the like, to a relatively small profile and then allowed to return to their original shape within the eye.

A useful technique for inserting an IOL into the eye includes use of an IOL injector or cartridge. Injectors for delivering IOLs into the eye typically employ a handpiece and a cartridge having a hollow insertion tube or cannula through which the folded IOL is passed using a pushrod. The cartridges are made of disposable materials, such as plastics, and remain in a sterile package until ready for coupling with the handpiece. Some injectors do without the cartridge, and may be reusable.

Conventional IOL cartridges include a load chamber connected to an injection tube. In many popular versions, such as in U.S. Pat. No. 4,681,102 to Bartell or U.S. Pat. No. 5,702,402 to Brady, the load chamber is formed by two hinged halves which receive the IOL, and which close to fold the IOL. A non-folding cartridge is seen in U.S. Pat. No. 5,474,562 to Orchowski in which forceps are used to insert the IOL into a proximal or rear opening of the cartridge. The injection tube includes a small diameter distal end that is insertable into the incision within the eye. After mating the cartridge with the handpiece (if a separate cartridge is used), the pushrod urges the IOL through the load chamber and through the injection tube into the eye. The distal end of the cartridge is beveled into a sharp point that enables insertion through the corneal incision and facilitates expulsion and manipulation of the IOL into the capsular bag. However, sometimes the IOL or the cartridge tip is damaged during the process of forcing the IOL through the cartridge tube In view of the above, there is a need for a cartridge that will not damage the IOL and is more robust than earlier designs.

SUMMARY OF THE INVENTION

The present application provides an intraocular lens (IOL) injector cartridge having an atraumatic tip. The cartridge includes a main body having a proximal opening for receiving an IOL and a lumen that extends longitudinally to a distal end having a distal opening smaller than the IOL. Passage through the lumen compresses or rolls the IOL so that when the distal end is inserted through a small incision in the eye the IOL can be expelled into the capsular bag. The distal end of the cartridge is beveled with a leading tip in front of a trailing heel. The characteristics of the beveled end are such that damage to the IOL is reduced. The bevel may be straight or curved and includes a distal face defined by the thickness of the distal end between the lumen and an exterior surface. The distal face may be flush with the bevel or chamfered. An inner corner angle between the distal face and the lumen is >60° to reduce the chance of scratching the IOL as it passes out of the distal opening The exemplary cartridges disclosed herein for receiving and delivering an intraocular lens to the inner eye comprises a main body extending longitudinally from a proximal opening for receiving the intraocular lens to a distal end. A lumen extends from the proximal opening to the distal end which defines a distal opening that is smaller than the intraocular lens. The distal end is beveled as seen in side view with a leading tip below and opposite a trailing heel, and further defines a distal face between an exterior surface and the lumen.

In one embodiment, the distal face including at least one portion that is not flush with the beveled distal end as seen in side view. The beveled distal end may be a straight bevel or a curved bevel. The portion of the distal face that is not flush with the beveled distal end may be a chamfer formed in a cutout region. Alternatively, the distal face is not flush with the beveled distal end around its entire periphery. For instance, the entire distal face may be chamfered or rounded.

In another embodiment, the distal face forms an inner corner with a wall of the lumen at the trailing heel having an angle $\phi \geq 60°$, and preferably $\phi \geq 90°$. In a further embodiment, the distal face includes at least one portion that is rounded. If the distal end has a curved bevel as seen in side view, the bevel angle adjacent the leading tip is desirably greater than the bevel angle adjacent the trailing heel. In one embodiment, the bevel is a planar bevel as seen in side view, and the angle $\beta$ of the planar bevel is between about 20-30° such that a distal face forms an inner corner with a wall of the lumen at the trailing heel having an angle $\phi$ between about 60-70°.

BRIEF DESCRIPTION OF THE DRAWINGS

Features and advantages of the present invention will become appreciated as the same become better understood with reference to the specification, claims, and appended drawings wherein:

FIG. 1 is a perspective view of a prior art intraocular lens (IOL) inserter cartridge showing loading of an exemplary IOL from the rear end thereof;

FIG. 2A is a top plan view of the cartridge of FIG. 1, while FIG. 2B is a longitudinal sectional view through the cartridge illustrating progressive advancement of an IOL therethrough to a beveled distal end, and FIG. 2C is an enlargement of the distal end in section;

FIG. 3 is a side elevation view of the distal end of an alternative IOL cartridge of the present application having a shallower bevel angle;

FIGS. 4A-4C are perspective, elevational, and sectional views of the distal end of a further alternative IOL cartridge disclosed herein, while FIGS. 4D and 4E are enlargements of areas in FIG. 4C;

FIG. 5 is a perspective view partly in phantom of an alternative IOL cartridge of the present application having a variable chamfered edge at the beveled tip, while FIG. 5A is an enlarged view of the distal end;

FIGS. 6A-6D are different views of the variable chamfered edge bevel tip of the cartridge of FIG. 5, while FIGS. 6E and 6F are enlargements of areas in FIG. 6D;

FIG. 7 is a perspective view partly in phantom of another IOL cartridge of the present application having a variable chamfered edge at the beveled tip, while FIG. 7A is an enlarged view of the distal end;

FIGS. 8A-8D are different views of the variable chamfered edge bevel tip of the cartridge of FIG. 7, while FIGS. 8E and 8F are enlargements of areas in FIG. 8D;

FIG. 9 is a perspective view partly in phantom of another IOL cartridge of the present application having a more rounded edge at the beveled tip, while FIG. 9A is an enlarged view of the distal end;

FIGS. 10A-10D are different views of the rounded edge bevel tip of the IOL cartridge of FIG. 9, while FIGS. 10E and 10F are enlargements of areas in FIG. 10D;

FIGS. 11A and 11B are elevation and sectional views through a still further IOL cartridge tip having a curved tip with a step;

FIGS. 12A and 12B are perspective and elevation views through a still further IOL cartridge tip having a curved tip with a less pronounced step than in FIGS. 11A-11B.

DETAILED DESCRIPTION OF THE PREFERRED EMBODIMENTS

Figure 13A:
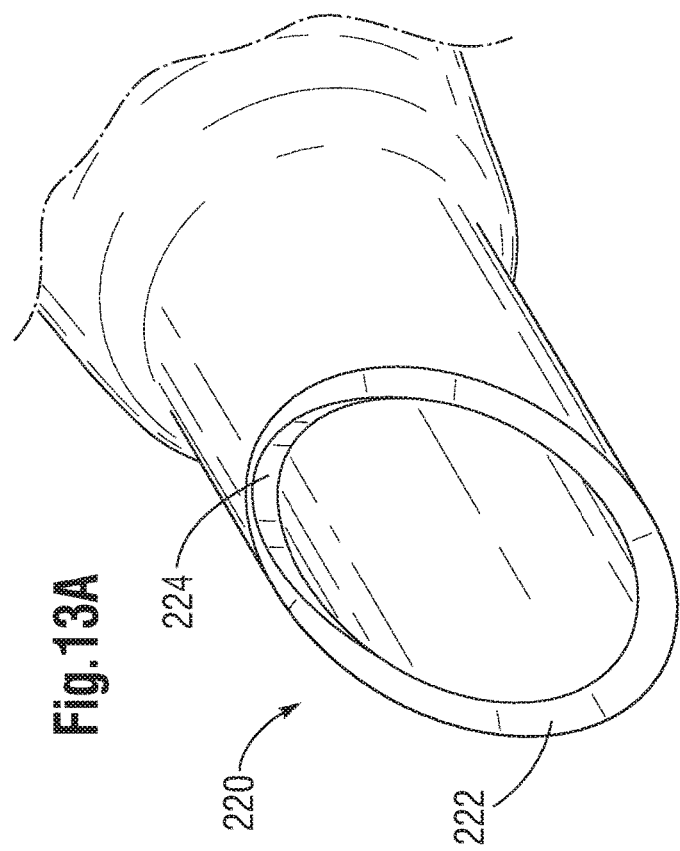
FIGS. 13A and 13B are perspective and elevation views through another IOL cartridge beveled tip with a partial cut out at the bevel heel.

FIGS. 1-2C illustrate an IOL cartridge 20 of the prior art which includes a main body 22 extending longitudinally from a proximal opening 24 to a distal end 26. A pair of webs project transversely outward from opposite sides of the main body 22 and terminate in a generally vertically-oriented finger grip 30a, 30b. The main body 22 of the cartridge 20 defines a gradually narrowing lumen or hollow interior 32 extending longitudinally from the proximal opening 24 to a distal opening 34 (FIG. 2B) at the distal end 26.

FIG. 1 illustrates an IOL held by tongs or forceps 50. This type of IOL includes a central disc-shaped optic 52, a leading haptic 54, and a trailing haptic 56. Typically, the optic 52 has opposed convex faces, although the present invention is not limited to cartridges for any particular type of IOL. The haptics 54, 56 are shown as thin arcuate members extending outward from opposite edges of the optic 52, and generally in the plane of the optic. The haptics 54, 56 curve in the same direction, in this case a counter-clockwise direction looking down on the IOL.

FIG. 2B shows the gradually narrowing lumen 32 from the proximal to the distal end of the cartridge 20, and the general shape of the IOL as it progresses through the main body 22. In particular, the cartridge 20, as with other such cartridges, provides a gradually narrowing lumen 32 that folds or otherwise compresses the IOL into a small profile so that it may be expelled through the distal opening 34 at the distal end 26 and through an incision into the eye. Intraocular lenses are inserted into the empty capsular bag left after removing the natural lens from the eye, typically due to opacification from conditions such as glaucoma. Folding the IOL through the cartridge enables a smaller incision to be used, which helps reduce trauma during the operation and recovery. However, folding and/or compressing the IOL generates significant compressive stresses in the IOL, which is restrained by the surrounding cartridge tube. The outward forces from the IOL against the tube lumen 32 and opposite inward reaction forces from the lumen on the IOL are alleviated at the moment the IOL emerges from the distal opening, and sometimes the sharp edges of the distal end cause damage to the IOL.

The shape of the distal end 26 facilitates introduction of the IOL into the eye and into the capsular bag. More particularly, the distal end 26 defines the termination of the generally tubular main body 22 and features a planar bevel angle β that results in a pointed leading tip 36 diametrically opposed to a trailing heel 38, such as seen in FIG. 2C. Due to the planar bevel, the side portions of the distal end 26 extend in half-ovals between the leading tip 36 and a trailing heel 38. The pointed leading tip 36 helps the surgeon open up the incision and extend the distal end 26 into the eye and into the capsular bag, while the relief provided by the bevel angle β allows the IOL to emerge more gradually from the tip than if the tube was cut off straight, or perpendicular to the central axis. Moreover, the end 26 may be rotated about its axis to allow the surgeon to reposition the heel 38 and thus "aim" the cartridge tip so that the IOL is expelled properly into the capsular bag. The planar beveled end 26 as shown typically has a bevel angle β of about 55° which is conventional in the art and provides adequate level of control for the surgeon. It should be noted that the bevel angles discussed herein refer to the angle (if there is a single angle) taken from a vertical plane (perpendicular to the central axis of the tubular main body 22) to the distal end 26, indicated in FIG. 2C. Consequently, a 0° bevel angle is one which is perpendicular to the central axis, or completely blunt and not beveled at all, and thus does not exist as it does not work. Conversely, the distal end becomes increasingly sharp at higher bevel angles, and angles above 45° are impractically long and do not exist either. Known bevels are between 40-55°.

Certain problems in the use of cartridges with planar bevels have been noted by the applicants. It should be understood that a "planar bevel" refers to a distal end 26 that defines a forward-looking distal face that lies exclusively in the plane of the bevel angle, or is flush with the bevel. The distal face of the distal end 26 is that surface formed by the thickness of the distal end that extends between the outer 40 and inner 42 tubular walls of the cartridge 20 (FIG. 2C). The entire distal face of the distal end 26 across the wall thickness of the cartridge 20 thus lies flush in a common plane along the bevel angle. This can also be termed a flush distal face because it lies flush within the contour of the distal end as seen from the side (FIG. 2C). Consequently, the trailing heel 38 of the distal end 26 forms the same sharp angle at the inside wall 42. As a result, as the IOL emerges from within the tubular lumen 32, the sharp inner corner angle of the heel 38 sometimes causes cuts or scratches on the expanding IOL, which are sometimes referred to as chatter marks.

Moreover, because of the sharp angle at the heel 38, the outward pressure imparted by the passing IOL sometimes creates splits in the cartridge material. That is, the sharp angle at the heel 38 presents an area of concentrated stress in the material which can sometimes split, potentially leading to loss of control of the delicate placement process. Furthermore, advances in the field of IOL implantation are driving the diameter of the cartridge distal tips ever smaller, which further reduces the strength of the distal tip. At some point, the strength limit of the distal tip is reached which limits its minimum size. Currently, the smallest distal tips having a planar bevel are 1.6 mm in diameter, with a wall thickness of 0.0016 mm.

The present application provides a number of solutions to help eliminate damage to either the IOL or the cartridge end 26. One solution shown in FIG. 3 involves a cartridge 60 having a distal end 62 with a planar bevel having a much shallower bevel angle β, such as approximately 30°, or less. More particularly, the bevel angle β is preferably between about 20-30°. By virtue of the shallower bevel angle, the distal face at the heel 66 of the distal end 62 also forms a shallower inner corner angle at the inside wall, thus reducing the potentially damaging sharp edge and also the stress concentration at that point. More specifically, for bevel angles β between 20-30°, the distal face forms an inner corner with a wall of the lumen at the trailing heel 66 that is between 60-70°.

Another alternative IOL cartridge 70 is seen in FIGS. 4A-4C, and includes a distal end 72 that forms a straight bevel angle β of about 65°, much like those in the prior art. A distal face 74 formed by the thickness of the distal end 72 between an outer wall 76 and an inner wall 78 defines the forward-looking end of the cartridge. An outer edge 80 of the distal face 74 lies in and defines the plane of the bevel angle β, preferably about 40-45°. Since the bevel as seen from the side as in FIG. 4B is straight, this configuration can be denoted a straight bevel. A planar bevel as described above is a subset of straight bevels. However, instead of being a planar bevel, the distal face 74 is angled or chamfered such that not all of it lies in the plane of the bevel angle β. In particular, an inner edge 82 of the distal face 74 does not lie in the plane of the bevel angle β. Another way to describe the distal face 74 is that it does not lie flush within the bevel plane.

With reference to FIGS. 4A and 4C, the distal end 72 has a variable chamfer around its circumference. As seen best in the enlargement of FIGS. 4D and 4E, the angle of the distal face 74 (face angle) changes from an angle θ that is greater than the bevel angle (i.e., sharper) at a leading tip 84 (See FIG. 4D) to one that is more blunt than the bevel angle at a trailing heel 86. As before, the leading tip 84 is diametrically opposed around the distal end 72 from the trailing heel 86. The face angle around the distal end 72 is that angle the distal face 74 makes with a plane perpendicular to the tubular axis as seen in any longitudinal section through the distal end (such as seen in FIGS. 4C-4E with a vertical longitudinal section). In the illustrated embodiment, the face angle at the heel 86 is 0°, as seen in FIG. 4E. Consequently, the inner edge 82 of the distal face 74 at the trailing heel 86 forms an inner corner angle φ, of about 90° at the intersection with the cartridge inner wall 78. This removes the sharp edge at the heel 86 which reduces the chance of damaging the IOL as it expulses from the distal end 72. Another way to state this solution is that the inner corner angle φ, at the trailing heel 86 is decoupled from the bevel angle β, which is not the case with a planar bevel.

Various side and sectional views seen in the present application are depicted with the leading tip 84 directly below the trailing heel 86, or vice versa, which simplifies depiction of the particular beveled distal end because of the traditional symmetry about a central plane that extends through the leading tip and trailing heel. However, it should be understood that asymmetric distal ends are not excluded unless explicitly stated herein for particular embodiments.

Now with reference to FIGS. 5 and 5A, a still further alternative IOL cartridge 90 is shown. The cartridge 90 is configured differently than that described above, though it is still adapted to receive an IOL and then mate with an inserter (not shown) for injection into an eye. Although the majority of the cartridge 90 is not particularly relevant to the disclosure of the present invention, and thus is shown in phantom, it typically includes a proximal body 92 having a proximal opening 94 in the form of a channel for receiving an IOL. A tubular nose 96 aligned with the opening 94 extends distally from the body 92 and terminates at a distal end 100. As with the earlier embodiment, the distal end 100 defines an opening that is smaller than the IOL such that as the IOL progresses distally from the proximal opening 94 is folded or otherwise compressed into a rolled configuration.

The distal end 100 is shown in greater detail in FIGS. 6A-6F, and defines a straight bevel angle β as seen in FIG. 6D, preferably about 40-45°. Once again, an outer edge 102 of a distal face 104 lies in and defines the bevel plane. The distal face 104 extends between an outer cartridge wall 106 and an inner cartridge wall 108 that defines the tube lumen. Again in contrast to a planar bevel, the distal face 104 has a chamfer angle that does not lie flush in the bevel plane.

As best seen in FIGS. 5A and 6D, an inner edge 110 of the distal face 104 is recessed into the lumen. At a leading tip 112 of the bevel, as seen in FIG. 6E, the distal face 104 makes a chamfer angle θ that is larger than the bevel angle. At a trailing heel 114, diametrically opposed to the leading tip 112 as seen in FIG. 6F, the distal face 104 makes a chamfer angle α that is also larger than the bevel angle, and in the opposite direction. It should be noted that a chamfer at the trailing heel 114 which forms an angle opposite to the bevel angle and is greater than 0° (such as in FIG. 4E) results in an obtuse inner corner angle φ. The angle θ may be equal to the angle α or one may be larger than the other. In a preferred embodiment, the distal face chamfer angle θ at the leading tip 112 is equal to the distal face chamfer angle α at the trailing heel 114, and they both are between about 70-80°. Although the trailing chamfer angle α may be as small as 0°, such as in the embodiment of FIGS. 4A-4E, it is desirably greater than 30° to result in an obtuse inner corner angle. Both the leading tip 112 and trailing heel 114 therefore define sharp points at their outer edges 102, but relatively shallow (obtuse) inner corner angles at their inner edges 110. These shallow corner angles serve two purposes: first, there is little chance of the inner edges 110 causing damage to the passing IOL, and second, the material at the inner edges 110 experiences no stress concentration which might lead to tearing.

A still further alternative distal end 120 for an IOL cartridge 90 is shown in FIGS. 7-8. The IOL cartridge 90 may be similar to that shown in FIG. 5, or may be another configuration such as that shown in FIG. 1. Once again, the majority of the cartridge 90 is not particularly relevant to the disclosure of the present invention, and thus is shown in phantom.

The distal end 120 is shown in greater detail in FIGS. 7A and 8A-8F, and defines a straight bevel angle β as seen in FIG. 8D, preferably about 40-45°. Once again, an outer edge 122 of a distal face 124 lies in and defines the bevel plane. The distal face 124 extends between an outer cartridge wall 126 and an inner cartridge wall 128 that defines the tube lumen. Again, in contrast to a planar bevel, the distal face 124 has a chamfer angle that does not lie flush in the bevel plane. The distal end 120 is similar to the distal end 100 of FIGS. 5-6, though one difference is that the extension of the tubular nose 96 of the cartridge 90 becomes gradually more elliptical, or more like a rounded rectangle. This configuration may accommodate the IOLs somewhat better as the optic portion assumes a more flattened as opposed to rolled tubular shape.

As best seen in FIGS. 7A and 8D, an inner edge 130 of the distal face 124 is recessed into the lumen. At a leading tip 132 of the bevel, as seen in FIG. 8E, the distal face 124 makes a chamfer angle θ that is larger than the bevel angle. At a trailing heel 134, as seen in FIG. 8F, the distal face 124 makes a chamfer angle α that is opposite the bevel angle. The angle θ may be equal to the angle α or one may be larger than the other. In a preferred embodiment, the distal face chamfer angle θ at the leading tip 132 is greater than the distal face chamfer angle α at the trailing heel 134. For instance, the leading chamfer angle θ is between about 70-80°, while the trailing chamfer angle α is between about 60-70°. Once again, it should be noted that the trailing chamfer angle α may be as small as 0°, such as in the embodiment of FIGS. 4A-4E, though it is desirably greater than 30° to result in an obtuse inner corner angle. Both the leading tip 132 and trailing heel 134 therefore define sharp points at their outer edges 122, but relatively shallow (obtuse) inner corner angles at their inner edges 130. These shallow corner angles reduce the chance of the inner edges 130 causing damage to the passing IOL, and reduce the stress concentration in the distal end 120 which might lead to tearing.

FIG. 8F also shows a somewhat different trailing heel 134 than in earlier embodiments. The distal face 124 at that point does not intersect the outer cartridge wall 126, but instead terminates at its outer edge 122 a short way down the straight bevel. Another way to state this is that the distal face 124 at the trailing heel 134 does not pass through the intersection of the bevel with the outer cartridge wall 126. This results in a short length of added material at the sharp point of the outer cartridge wall 126 which helps strengthen the wall and avoids tearing during expulsion of the compressed IOL.

A still further alternative distal end 140 for an IOL cartridge 90 is shown in FIGS. 9-10. Once again, the IOL cartridge 90 may be similar to that shown in FIG. 5, or may be another configuration such as that shown in FIG. 1. The distal end 140 is shown in greater detail in FIGS. 9A and 10C-10F, and once again defines a straight bevel angle β as seen in FIG. 10D, preferably about 40-45°. An outer edge 142 of a distal face lies in and defines the bevel plane. As before, the distal face extends between an outer cartridge wall 144 and an inner cartridge wall 146 that defines the tube lumen. In contrast to a planar bevel, the distal face does not lie flush in the bevel plane, but in this configuration there is no single chamfer but a more rounded face from the trailing heel 148 to the leading tip 150 and in between.

As best seen in FIG. 10E, at a leading tip 150 of the bevel the distal face extends between an outer edge 152 and an inner edge 154 and forms a rounded face 156. At the trailing heel 148, as seen in FIG. 10F, the distal face forms a rounded face 158. These rounded faces 156, 158 may have similar curvatures, though due to their different geometries the rounded face 158 at the trailing heel 148 extends around a greater arc than the face 156 at the leading tip 150. The result is a smooth surface around the distal end 140 of the cartridge 90, which eliminates any sharp edges and corresponding danger of scratching the IOL. It should be noted that a rounded distal face is not flush with the particular bevel, much like the earlier-described chamfers.

Now with reference to FIGS. 11A-11B, a slightly different cartridge distal end 170 is shown. As before, the distal end 170 is pointed with a leading tip 172 and a trailing heel 174. However, instead of the straight bevel, the distal end 170 has a curved bevel, with a relatively shallow curvature 176 adjacent the leading tip 172 gradually increasing to a step 178 adjacent the trailing heel 174. In the illustrated embodiment, the angle of the curved bevel at the trailing heel 174 is about 0°. Desirably, the bevel angle adjacent the leading tip 172 is greater than the bevel angle adjacent the trailing heel 174. This "curved bevel" is not strictly a bevel, but the terminology will be used to indicate its proximity to a straight bevel. In other words, as used herein, a beveled end refers to both straight and curved bevels, wherein both include a leading tip opposed to a trailing heel. Also as mentioned above, a preferred configuration provides symmetry about a central plane through a diametrically opposed leading tip 172 and trailing heel 174, though asymmetric configurations are contemplated.

Furthermore, the distal face is flush with the curved bevel, meaning that the entire distal face lies in the curvature of the distal end 170 as seen from the side in FIG. 11A. Consequently, as seen in FIG. 11B, the distal face has a 90° inner corner angle 180 at the trailing heel 174, much like the embodiment of FIGS. 4A-4C. Once more, this reduces the potential for damaging IOL as it passes out of the lumen of the cartridge end 170. Of course, the distal face need not lie flush within the curvature of the distal end 170, and may be chamfered as described in several embodiments above.

FIGS. 12A-12B illustrate a still further cartridge distal end 190 having a curved bevel. In particular, the curved bevel extends between a leading tip 192 and a trailing heel 194. As with the embodiment of FIGS. 11A-11B, the distal face lies flush with the curvature of the curved bevel. As before, the bevel angle adjacent the leading tip 192 is greater than the bevel angle adjacent the trailing heel 194. However, the curvature is modified, with a shallow arc 196 adjacent the leading tip 192 which transitions into a less pronounced step 198 adjacent to the trailing heel 194. This configuration results in a slightly acute inner corner 200 at the trailing heel 194, as seen in FIG. 12B. As with the reduced bevel angle of the embodiment of FIG. 3, as long as the angle of the curved bevel at the trailing heel 194 is approximately 30° or less, the inner corner 200 will be sufficiently blunt to avoid damage to the passing IOL. In a preferred embodiment, the distal face forms an inner corner 200 with a wall of the lumen at the trailing heel 194 having an angle that is ≥60°. Indeed, several embodiments above described inner corner angles of 90° and greater, and the lower limit of 60° is considered to be the sharpest inner corner angle that can be utilized without creating significant risk of scratching the IOL.

Figure 13B:
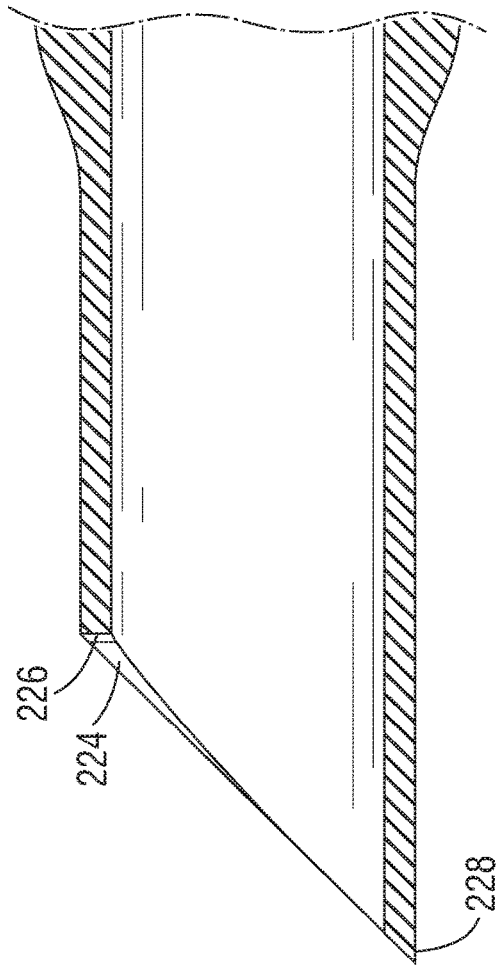

Finally, the cartridge distal end 220 shown in FIGS. 13A-13B includes a partial planar bevel. More particularly, a majority of the distal face 222 lies flush with the plane of the bevel, which may be 40-45°, but is interrupted by a scoop or cutout 224 at the trailing heel 226. In other words, as seen in FIG. 13B, the distal face 222 extends from a leading tip 228 up into proximity with the trailing heel 226, but is interrupted by the cutout 224. The cutout 224 extends a short distance down around the distal end 220, such as about 30° symmetrically from a central vertical plane. The cutout 224 may be formed at an angle perpendicular to the central axis of the tubular cartridge distal end 220, as shown, or may be slightly angled toward the bevel (up to about 30°)

or even chamfered in an opposite direction to the bevel. The result is an inner corner angle that is less likely to scratch or otherwise damage the passing IOL. Moreover, the remaining portion of the distal end can remain as a planar bevel, which maintains ease of cartridge tip insertion into the wound and is proven effective in delivering the IOL. In the illustrated embodiment the inner corner angle is 90°. The cutout 224 can be viewed as an abbreviated chamfer in contrast to the variably chamfered embodiments described above.

The various solutions for cartridge distal ends provided herein permit the distal ends to have diameters down to about 1.4 mm, with a wall thickness of about 0.014 mm. Materials used for the IOL cartridges described herein include polypropylene, polycarbonate, polyurethane or other appropriate thermoplastics. The various shapes for the distal ends can be formed by molding or laser cutting. In particular, the variable chamfer geometries are especially well-suited to injection molding.

While the invention has been described in its preferred embodiments, it is to be understood that the words which have been used are words of description and not of limitation. Therefore, changes may be made within the appended claims without departing from the true scope of the invention.

What is claimed is:

1. A cartridge for receiving and delivering an intraocular lens to the inner eye, the intraocular lens having an optic with a diameter, comprising:
   a main body extending longitudinally from a proximal opening sized to receive the optic of the intraocular lens to a tubular distal end having a diameter of less than 1.6 mm, the main body being formed of a material selected from the group consisting of polypropylene, polycarbonate and polyurethane, and the main body having a lumen extending from the proximal opening to the distal end which defines a distal opening that is smaller than the proximal opening and smaller than the optic diameter such that passage of the IOL through the lumen causes the optic to fold into a rolled configuration, the distal end being beveled as seen in side view with a leading tip below and opposite a trailing heel, the beveled distal end defines a bevel angle line drawn between the leading tip and trailing heel that forms a bevel angle $\beta$ with a longitudinal axis of the main body, the distal end further defining a distal face between an exterior surface and the lumen, wherein at least a portion of the distal face around the distal end is not flush with the beveled distal end as seen in side view.

2. The cartridge of claim 1, wherein the beveled distal end defines a straight bevel.

3. The cartridge of claim 1, wherein the portion of the distal face that is not flush with the beveled distal end includes a chamfer formed in a cutout region, and the rest of the distal face is flush with the beveled distal end.

4. The cartridge of claim 1, wherein a trailing chamfer angle $\alpha$ formed by the chamfer formed in a cutout region is about 0°.

5. The cartridge of claim 1, wherein the distal face is not flush with the beveled distal end around its entire periphery.

6. The cartridge of claim 5, wherein the entire distal face is chamfered.

7. The cartridge of claim 6, wherein the distal face forms an inner corner with a wall of the lumen at the trailing heel having an angle $\phi \geq 60°$.

8. The cartridge of claim 6, wherein the bevel angle adjacent the leading tip is greater than the bevel angle adjacent the trailing heel.

9. The cartridge of claim 8, wherein the bevel angle adjacent the trailing heel is about 0°.

10. The cartridge of claim 5, wherein the entire distal face is rounded.

11. The cartridge of claim 1, wherein the distal face forms an inner corner with a wall of the lumen at the trailing heel having an angle $\phi \geq 90°$.

12. The cartridge of claim 1, wherein an outer edge of the distal face defines a sharp edge and lies in and defines the beveled distal end.

13. The cartridge of claim 12, wherein the distal face has a chamfer between the outer edge and the lumen that defines a trailing chamfer angle $\alpha$ at the trailing heel between about 70-80° and forms an inner corner with a wall of the lumen at the trailing heel having an obtuse inner corner angle $\phi$, such that the trailing heel defines a sharp point at its outer edge and an obtuse angle at its inner edge.

14. The cartridge of claim 12, wherein the distal face has a chamfer between the outer edge and the lumen that defines a trailing chamfer angle $\alpha$ at the trailing heel, and the distal face at the trailing heel does not pass through the intersection of the bevel angle line with the outer cartridge wall so as to have a short length of added material thickness at the sharp edge of the trailing heel.

15. The cartridge of claim 14, wherein the trailing chamfer angle $\alpha$ is between about 70-80°.

16. The cartridge of claim 1, wherein the lumen is circular in perpendicular cross-section at the distal end such that a wall thickness is constant around the tubular distal end.

17. The cartridge of claim 1, wherein the distal face includes the chamfer around its entire periphery that is not flush with the beveled distal end, such that both the leading tip and trailing heel define sharp points at their outer edges and obtuse inner corner angles at their inner edges.

18. The cartridge of claim 1, wherein the beveled distal end defines a straight bevel having the bevel angle $\beta$, and the distal face defines a leading chamfer angle $\theta$ at the leading tip that is greater than the bevel angle $\beta$.

19. The cartridge of claim 18, wherein the distal face defines a trailing chamfer angle $\alpha$ at the trailing heel that is greater than the bevel angle $\beta$.

* * * * *